(12) United States Patent
Hatami et al.

(10) Patent No.: US 11,144,657 B2
(45) Date of Patent: Oct. 12, 2021

(54) SYSTEM AND METHOD OF PROVIDING A SECURE INTER-DOMAIN DATA MANAGEMENT USING BLOCKCHAIN TECHNOLOGY

(71) Applicant: Motion Matters Inc., Fairfax, VA (US)

(72) Inventors: Naquib Hatami, Fairfax, VA (US); Zalmai Azmi, Centreville, VA (US)

(73) Assignee: MOTION MATTERS INC., Fairfax, VA (US)

( * ) Notice: Subject to any disclaimer, the term of this patent is extended or adjusted under 35 U.S.C. 154(b) by 355 days.

(21) Appl. No.: 16/432,618

(22) Filed: Jun. 5, 2019

(65) Prior Publication Data

US 2020/0125750 A1 Apr. 23, 2020

Related U.S. Application Data

(60) Provisional application No. 62/749,532, filed on Oct. 23, 2018.

(51) Int. Cl.
   *G06F 21/62* (2013.01)
   *H04L 29/06* (2006.01)
   *G16H 10/60* (2018.01)

(52) U.S. Cl.
   CPC ...... *G06F 21/6209* (2013.01); *G06F 21/6245* (2013.01); *G16H 10/60* (2018.01); *H04L 63/104* (2013.01); *H04L 63/105* (2013.01)

(58) Field of Classification Search
   CPC . G06F 21/6209; G06F 21/6245; G16H 10/60; H04L 63/104; H04L 63/105
   USPC .......................................................... 713/165
   See application file for complete search history.

(56) References Cited

U.S. PATENT DOCUMENTS

2020/0380156 A1* 12/2020 Garg ..................... H04L 63/061
2021/0006408 A1*  1/2021 Park ..................... H04L 9/0894

* cited by examiner

*Primary Examiner* — Jacob Lipman

(57) ABSTRACT

A system and method of providing a secure inter-domain data management platform based on blockchain technology allows a user to access files of one or more organizations based on the credentials of the user. The system includes at least one remote server and a network of computing nodes. The remote server is used to manage at least one group. The at least one group may be one or more intelligence or government organizations. The at least one group includes a plurality of member accounts. Each member account includes a member access level. The network of computing nodes is used to manage a blockchain system and to store a plurality of files. Each file includes a file access level. A user with a member account can access a file in accordance to the member access level of the member account and the file access level of the file.

15 Claims, 18 Drawing Sheets

SYSTEM AND METHOD OF PROVIDING A SECURE INTER-DOMAIN DATA MANAGEMENT USING BLOCKCHAIN TECHNOLOGY

The current application claims a priority to the U.S. Provisional Patent application Ser. No. 62/749,532 filed on Oct. 23, 2018.

FIELD OF THE INVENTION

The present invention relates generally to a field of data processing. More specifically, the present invention is a system and method that provides a secure inter-domain data management platform using blockchain technology.

BACKGROUND OF THE INVENTION

Conventional data and/or file management system generally lack in reliability, security, and/or configurability with regard to managing documents (such as exchanging videos, photos, textual documents etc.). Individuals and/or organizations may require abilities to share documents while at the same time also maintaining control and/or data protection for the shared documents. Further, sharing the documents with one or more individuals and/or organizations may increase a likelihood of unauthorized access of the document that may be detrimental for the organization that may be sharing the documents. For instance, a confidential document that may need to be shared digitally by one organization (such as CIA) with another organization (such as Interpol) may be prone to cyber attacks and/or prone to data loss due to server failure. As cyber-attacks evolve in new and/or more complicated ways, security organizations may have difficulty keeping up. Further, such cyber attacks, in an instance, may create a threat to organization's security and/or may cost billions of dollars. Further, the organizations may need a solution that could provide information sharing capabilities and/or would be reliable, secure, configurable, and easy to use at the same time.

Therefore, there is a need for improved systems and methods to facilitate data management based on blockchain technology that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

According to some embodiments, a flowchart of a method to facilitate a user to access a digital content from a blockchain file server based on a user access level is disclosed. The user access level may be, in an example specified by an administrator of the blockchain file server. Alternatively, and/or additionally, a submitting user uploading the digital content may also specify the user access level by way of an access policy. The access policy in general may be specific conditions under which access to the digital content is to be allowed. For example, the access policy may indicate one or more characteristics of a user authorized to access the digital content. For example, the one or more characteristics may include indication of a node (i.e. node identifier) on which the user is registered as a member, a hierarchical level associated with the user within an organization, a department within which the user operates, an identifier of the user and so on. Accordingly, access to the digital content may be limited to only such users who satisfy criterion specified in the access policy. Accordingly, the method may include a step of receiving, using a communication device, a sensory data from a user device to access a digital content from a blockchain file server. Further, the method may include a step of analyzing, using a processing device, the sensory data to determine a user access level associated with the user device. Further, the method may include a step of retrieving, using the processing device, the digital content from the blockchain file server based on the analyzing. Further, the method may include a step of transmitting, using the communication device, the digital content to the user device.

According to some aspects, a flowchart of a method to facilitate storing a user access level and a user role associated with a user in a database is disclosed. Accordingly, the method may include a step of receiving, using a communication device, a sensory data from a user device. Further, the method may include a step of analyzing, using a processing device, the sensory data. Further, the method may include a step of assigning, using the processing device, a user access level and a user role based on the analyzing. Further, the method may include a step of storing, using the processing device, the user access level and the user role on a database.

According to some aspects, a flowchart of a method to facilitate sharing of a digital content between a first user device and a second user device is disclosed. Accordingly, the method may include a step of receiving, using a communication device, a digital content from a first user device. Further, the method may include a step of assigning, using the processing device, an access level to the digital content. Further, the method may include a step of updating, using the processing device, a blockchain file server based on the assigning. Further, the method may include a step of receiving, using the communication device, a sensory data from a second user device to access the digital content. Further, the method may include a step of receiving, using the communication device, a sensory data from a second user device to access the digital content. Further, the method may include a step of determining, using the processing device, a user access level associated with the second user device based on the sensory data. Further, the method may include a step of retrieving, using the processing device, the digital content from the blockchain file server based on the determining. Further, the method may include a step of transmitting, using the communication device, the digital content to the user device.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

DETAIL DESCRIPTIONS OF THE INVENTION

All illustrations of the drawings are for the purpose of describing selected versions of the present invention and are not intended to limit the scope of the present invention.

Figure 1:
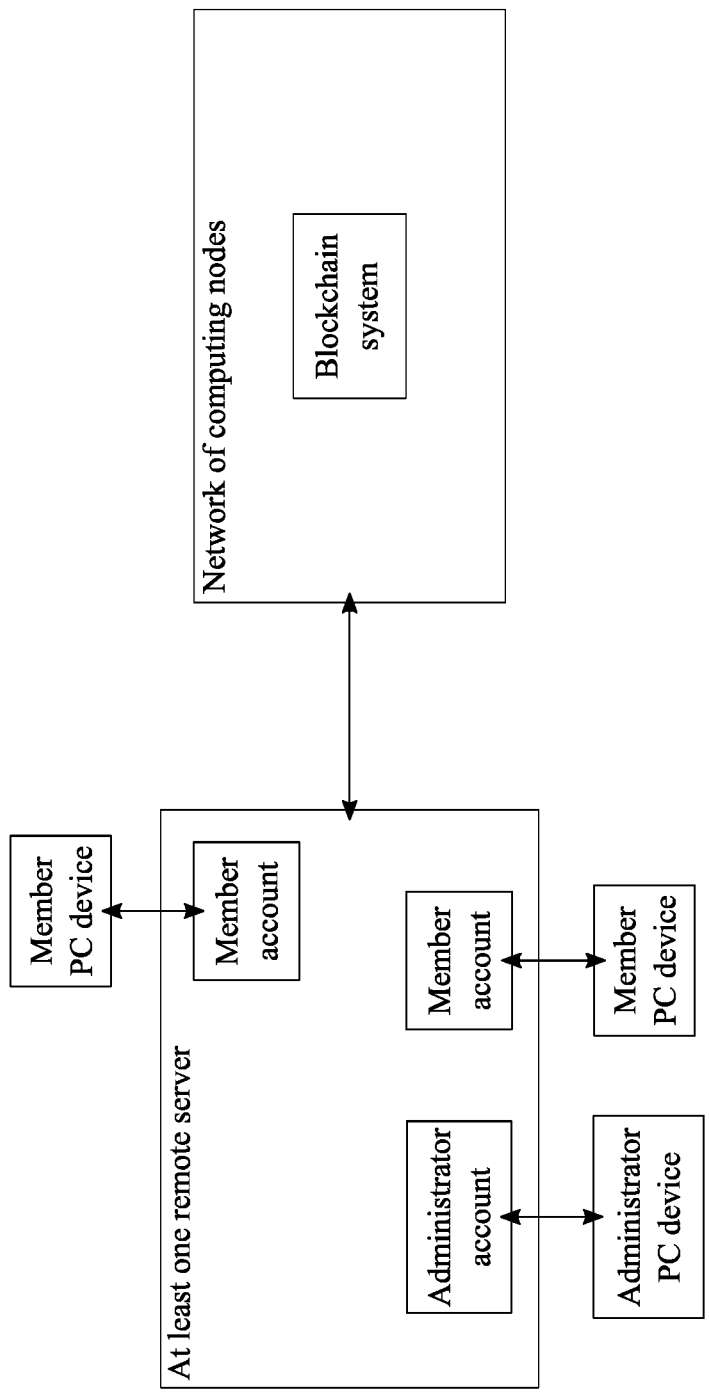
FIG. 1 is a block diagram of the system of the present invention.

In reference to FIGS. 1 through 17, the present invention is a system and method to facilitate data management based on blockchain technology. In further detail, the present invention is a software application used to access sensitive information which is encrypted through a blockchain system. In reference to FIG. 1, the system of the present invention is provided with at least one remote server and a network of computing nodes. The remote server is a centralized server used to manage at least one group (Step A). The at least one group may be an intelligence or government service organizations such as, but not limited to, the federal bureau of investigation (FBI), the central intelligence agency (CIA), or the department of defense (DOD). The at least one group includes a plurality of member accounts. The plurality of member accounts is a set of user accounts that allows a user to access and use the present invention. Each member account is associated with a corresponding member personal computing (PC) device and includes a member access level. Moreover, the remote server is used to store information provided by the plurality of member accounts and to manage the administrative processes of the present invention. The member PC device allows each user with a member account to interact with and use the present invention. The member PC device may be any type of computing device such as, but not limited to, a desktop computer, a smartphone, a mobile device, or an electronic tablet. The member access level is an assigned rank which determines what can be accessed by a user through the present invention. The network of computing nodes is a set of computing devices which is used to manage at least one blockchain system (Step B). Moreover, the network of computing nodes is used to store a plurality of files (Step C). The blockchain system includes a permission-based distributed ledger that allows a user to record or access the plurality of files onto or from the network of computing nodes. Further, the network of computing nodes is a blockchain file storage system which is a decentralized storage system where data is stored across multiple computing devices or servers. The plurality of files is set of files which can be any type of file such as, but not limited to, an audio file, a video file, or written document file. Each of the plurality of files includes at least one file access level. The at least one file access level is an assigned rank which is used to determine if a user can access a file from the plurality of files.

Figure 3A:
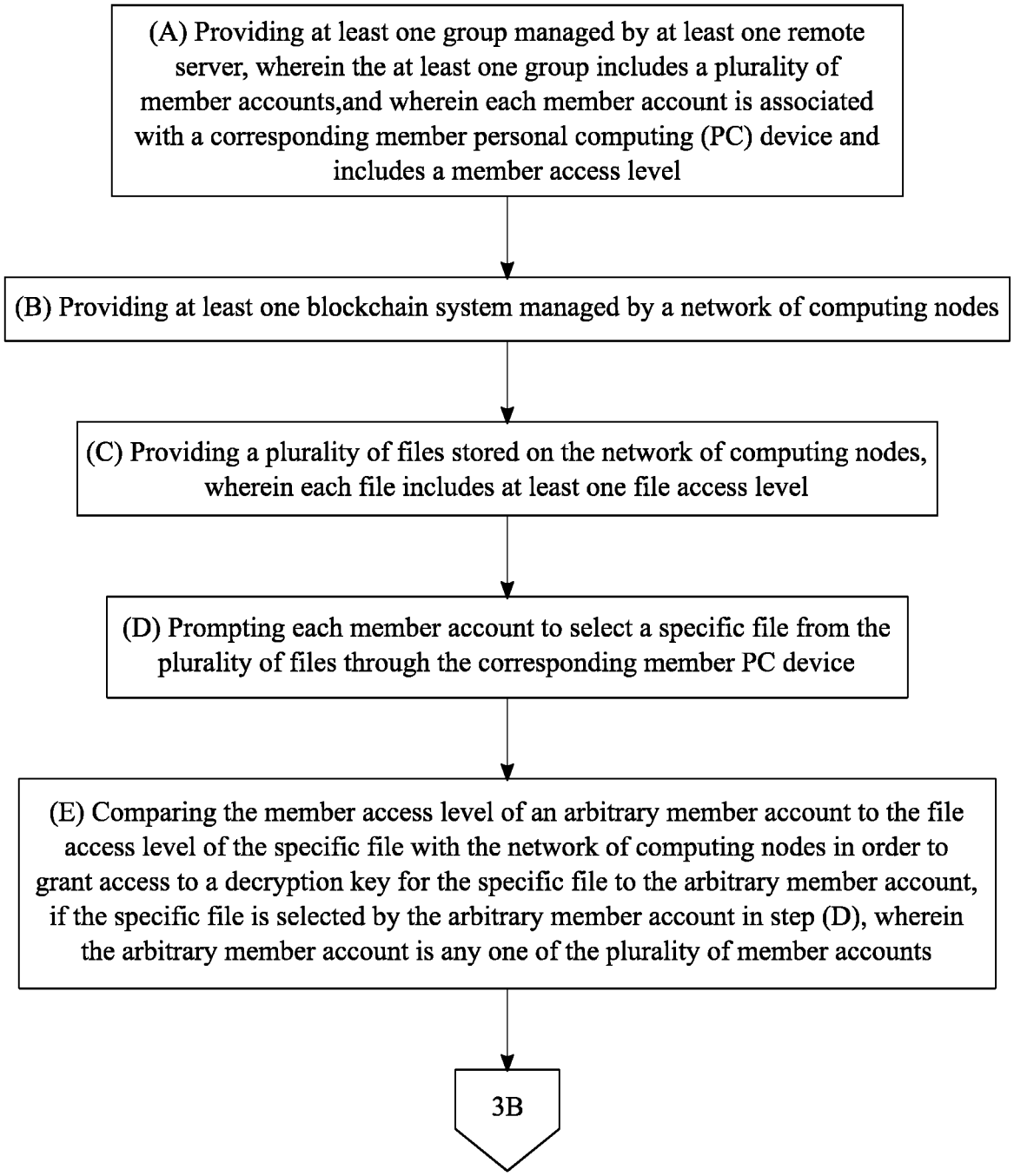
FIG. 3A is a flowchart illustrating the overall process of the present invention.
Figure 3B:
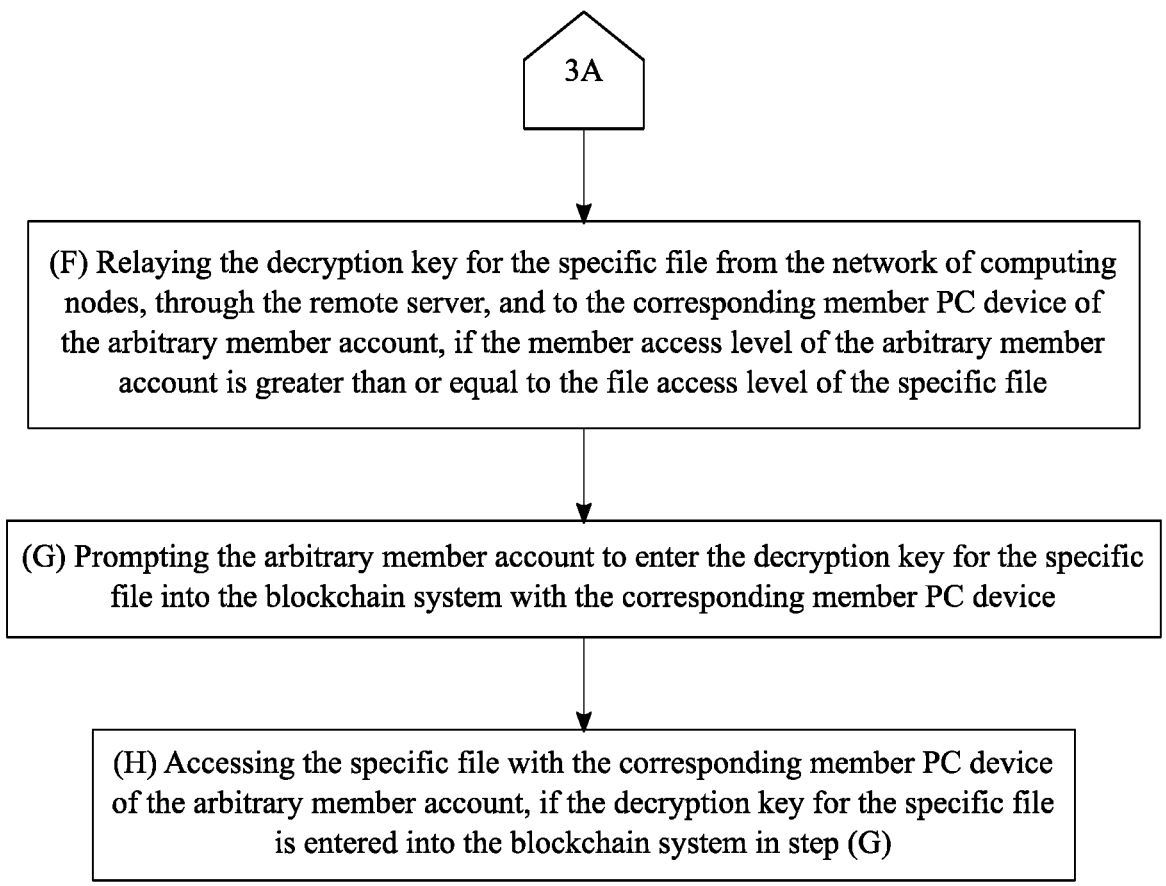
FIG. 3B is a continuation of the flowchart from FIG. 3A.

With reference to FIGS. 3A and 3B, the method of the present invention follows an overall process that provides a secure inter-domain data management using blockchain technology. Each member account is prompted to select a specific file from the plurality of files through the corresponding member PC device (Step D). In further detail, step D is a request to access the specific file from the plurality of files. In order to grant access to a decryption key for the specific file to an arbitrary member account, the network of computing nodes compares the member access level of the arbitrary member account to the file access level of the specific file (Step E). Step E is processed if the specific file is selected by the arbitrary member account in step D. The arbitrary member account is any one of the plurality of member accounts. Step E is processed to confirm if the arbitrary account has sufficient credentials to access the specific file. The decryption key is a specific parameter that determines the functional output of the specific file. The decryption key is then relayed from the network of computing nodes, through the remote server, and to the corresponding member PC device of the arbitrary member account (Step F). Step F is processed if the member access level of the arbitrary member account is greater than or equal to the file access level of the specific file. Thus, step F provides the arbitrary member account with the decryption key in order to access the specific file. The arbitrary member account is prompted to enter the decryption key for the specific file into the blockchain ledger with the corresponding member PC device (Step G). Thus, step G allows the arbitrary member account to enter the decryption key when desired in order to access the specific file. Further, the blockchain system can confirm or reject the decryption key based on the authenticity of the decryption key. The specific file is accessed with the corresponding member PC device of the arbitrary member account (Step H). Step H is processed if the decryption key for the specific file is entered into the blockchain ledger in step G. Further, step H is processed if the decryption key is successfully authenticated by the blockchain system. Thus, step H allows the arbitrary member to view the specific file on the corresponding member PC device. Moreover, the specific file can only be viewed and cannot be modified due to the features of the blockchain ledger.

Figure 2:
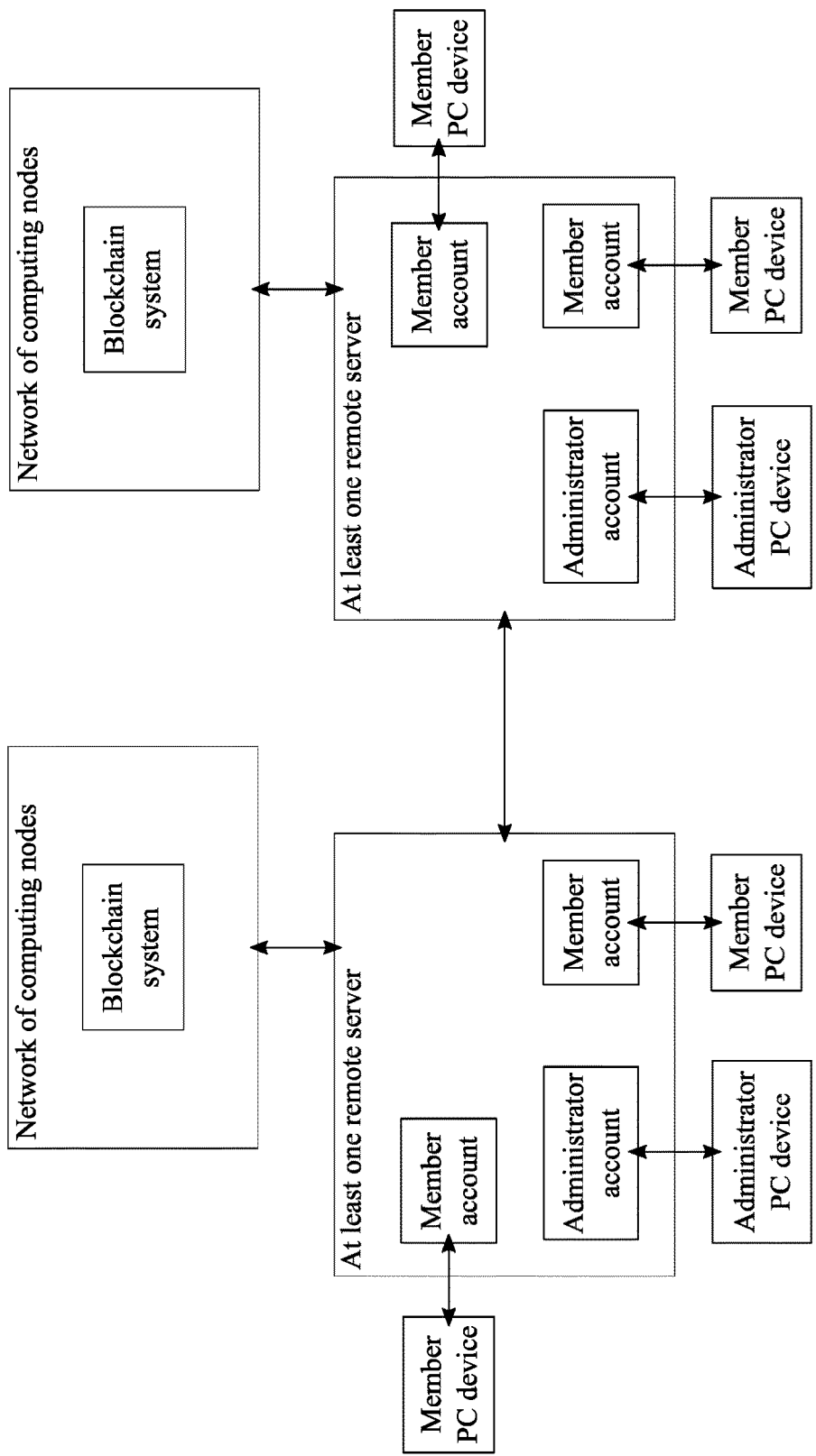
FIG. 2 is a block diagram of the system of the present invention with a plurality of groups.
Figure 4:
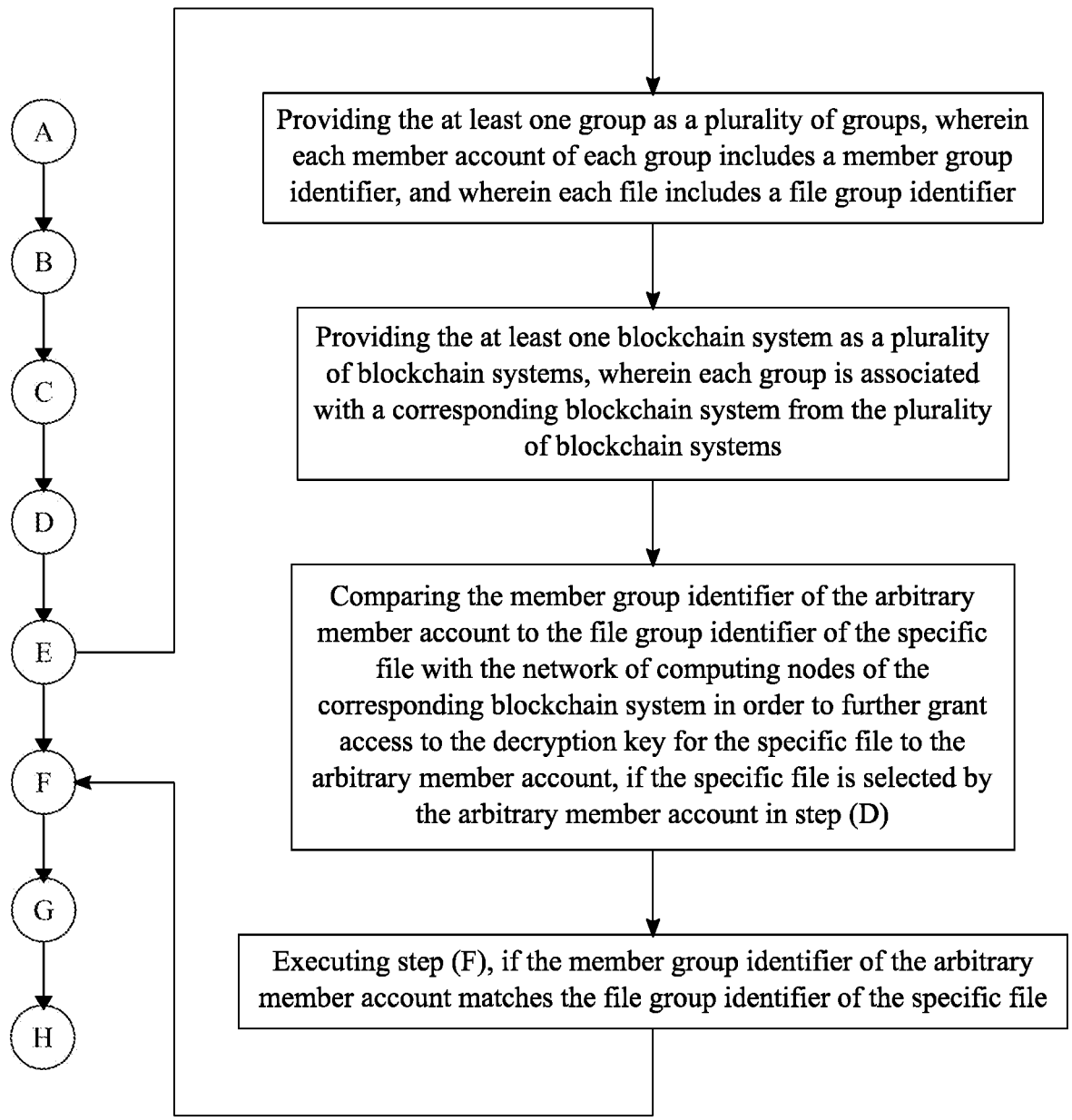
FIG. 4 is a flowchart illustrating the subprocess of verifying a member group identifier.

With reference to FIGS. 2 and 4, the following subprocess is used to further verify if the arbitrary member account meets the requirements to access the specific file. In order for multiple intelligence or government groups to share information amongst each other, the at least group is provided as a plurality of groups. Each member account of each group includes a member group identifier. Further, each file includes a file group identifier. The member group identifier is information used to identify which group is associated with a member account from the plurality of member accounts. Similarly, the file group identifier is information to identify which group is associated with a file from the plurality of files. Further, the at least one blockchain system is provided as a plurality of blockchain system. Each group is associated with a corresponding blockchain system from the plurality of blockchain systems. In further detail, each group such as, but not limited to, the CIA, the FBI or other intelligence or government organization is associated with their own remote server and network of computing nodes. Further, each blockchain system is managed by a corresponding network of computing nodes. In order to further grant access to the decryption key for the specific file to the arbitrary member account, the member group identifier of the arbitrary member account is compared to the file group identifier of the specific file with the network of computing nodes of the corresponding blockchain system. This step is processed if the specific file is selected by the arbitrary member account in step D. Further, this step is used to verify that the arbitrary member account meets the requirements to access the specific file. Step F is then executed if the member group identifier of the arbitrary member account matches the file group identifier of the specific file. This step is processed if the specific file and the arbitrary member account belong to the same member group which allows the arbitrary member account to access the file.

Figure 5:
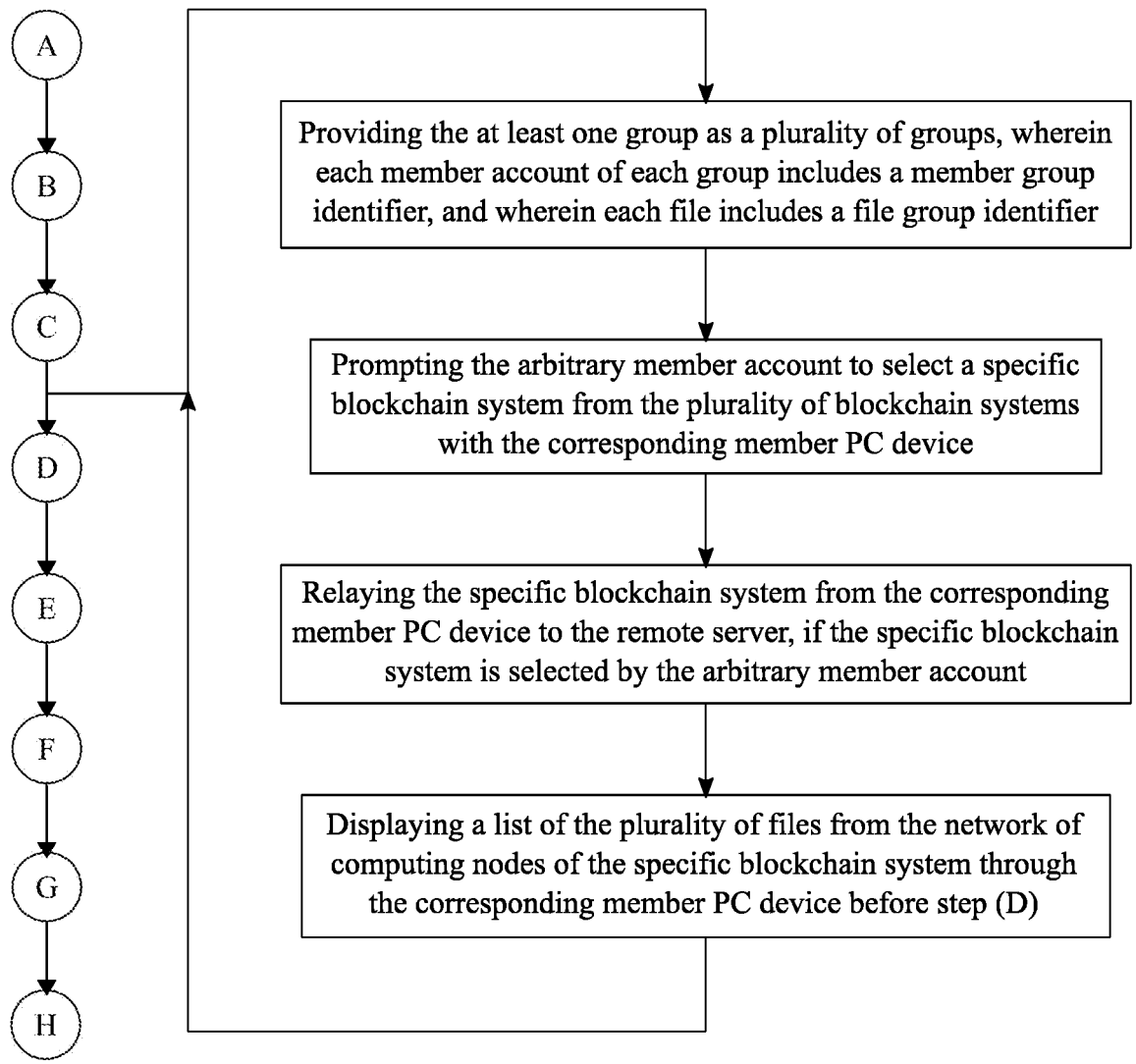
FIG. 5 is a flowchart illustrating the subprocess of selecting a file from the blockchain system of any group.

With reference to FIGS. 2 and 5, the following subprocess allows a user to access a file from the network of computing nodes of any group. The arbitrary member account is prompted to select a specific blockchain system from the plurality of blockchain systems with the corresponding member PC device. This step provides a user the option to choose a network of computing nodes of a particular group from the plurality of groups. A selection for the specific blockchain system is relayed from the corresponding member PC device to the remote server. This step is processed if the specific blockchain system is selected by the arbitrary member account. Further, this step notifies the remote server that a user is attempting to access the file storage system of a particular group. A list of the plurality of files from the network of computing nodes of the specific blockchain system is displayed through the corresponding member PC device before step D. This step allows a user to select the specific file from the file storage system of a particular group. For example, a user from the FBI is able to access a file that is stored on the file storage system of the CIA.

Figure 6:
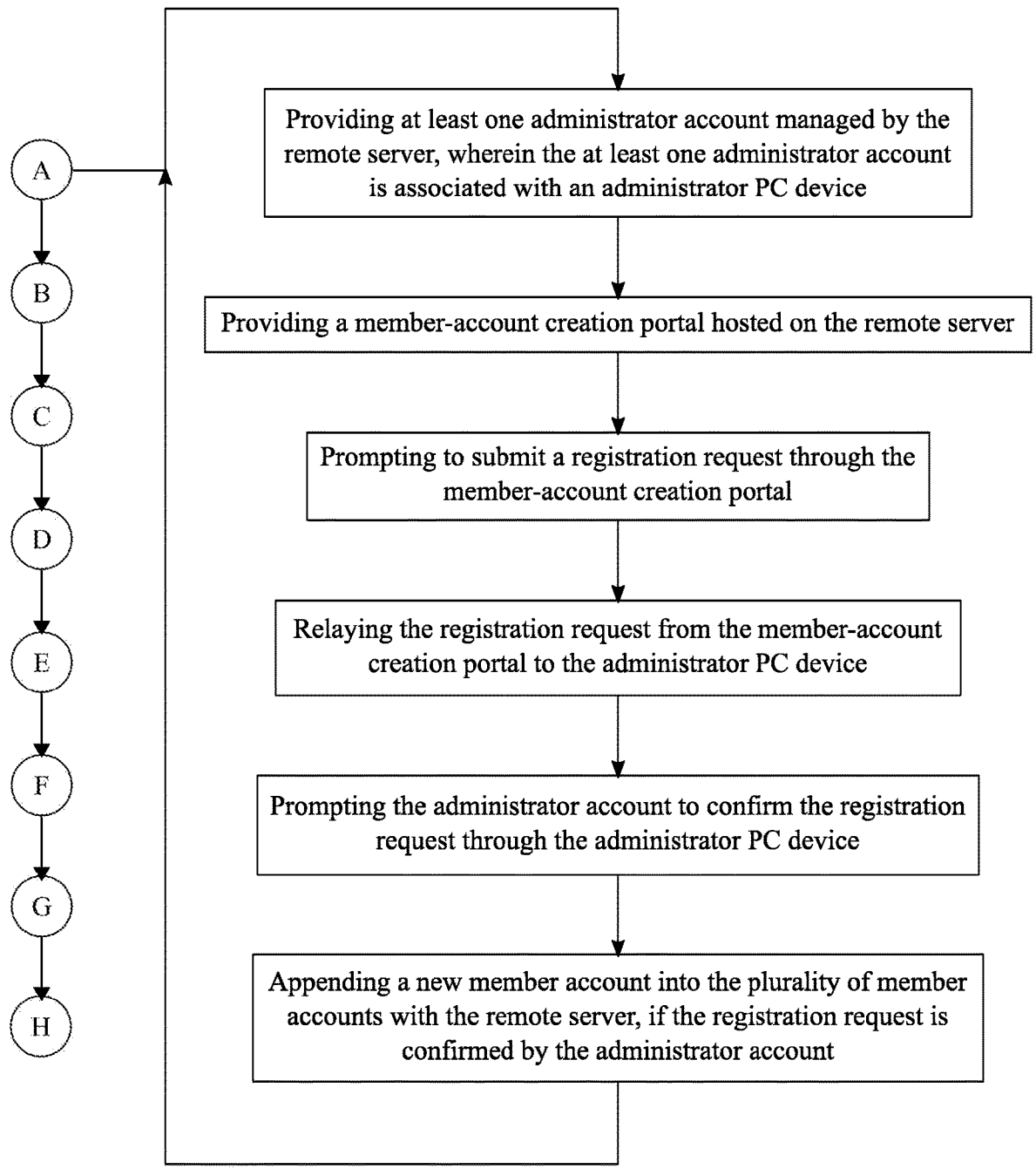
FIG. 6 is a flowchart illustrating the subprocess of creating a new member account.

With reference to FIG. 6, the following subprocess allows an administrator account to create a new member account. The remote server is used to manage at least one administrator account. The at least one administrator account is associated with an administrator PC device. The at least one administrator account is a user account that includes administrative privileges. The remote server is used to host a member-account creation portal. The member-account creation portal allows an individual to register for a member account on the present invention. An individual is prompted to submit a registration request through the member-account creation portal. This step is provided if an individual does not currently own a member account on the present invention. The registration request is relayed from the member-account creation portal to the administrator PC device. This step notifies the administrator account that an individual is attempting to create a member account. The administrator account is then prompted to confirm the registration request through the administrator PC device. This step allows the administrator account to confirm or deny the registration request based on the information provided by an individual attempting to create a member account. In further detail, a background check may be processed by the administrator in order to verify the creation of a new account. A new member account is appended into the plurality of member accounts with the remote server. This step is processed if the registration request is confirmed by the administrator account.

Figure 7:
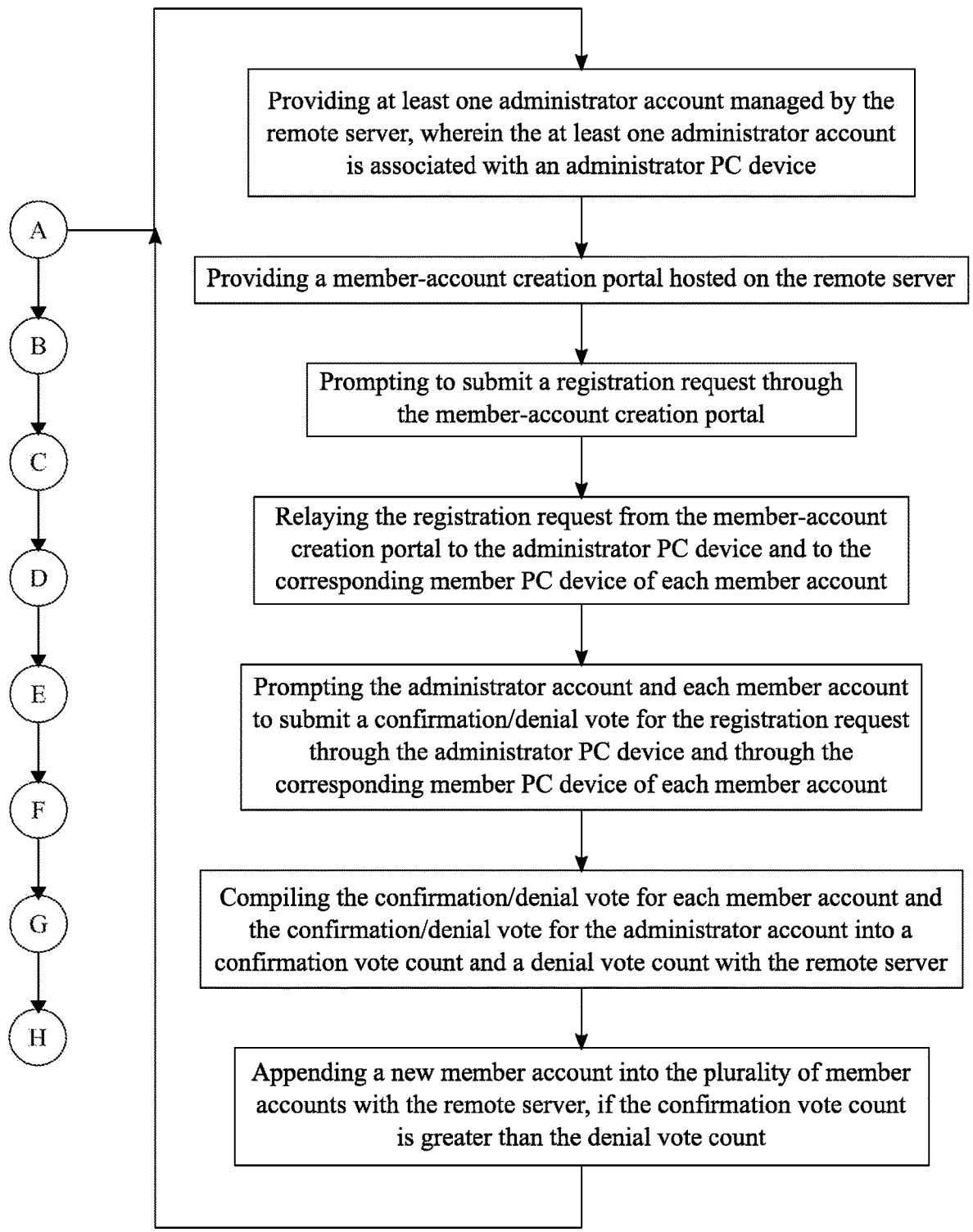
FIG. 7 is a flowchart illustrating the subprocess that allows each member account and the administrator account to vote on the creation of a new member account.

With reference to FIG. 7, the following subprocess allows the administrator account and each member account to vote for the creation of a new member account. An individual is prompted to submit a registration request through the member-account creation portal. The registration request is relayed from the member-account creation portal to the administrator PC device and to the corresponding member PC device of each member account. This step notifies the administrator account and each member account that an individual is attempting to create a member account. The administrator account and each member account are prompted to submit a confirmation/denial vote for the registration request through the administrator PC device and through the corresponding member PC device of each member account. This step allows the administrator account and each member account to vote whether or not an individual is allowed a member account. The confirmation/denial vote for each member account and the confirmation/denial vote for the administrator account is compiled into a confirmation vote count and a denial vote count with the remote server. The confirmation vote count is an aggregation of all the votes to confirm the registration request. The denial vote count is an aggregation of all the votes to deny the registration request. Thus, if the confirmation vote count is greater than the denial vote count, then a new member account is appended into the plurality of member accounts with the remote server. If the denial vote count is greater than the confirmation vote count, a new member account is not created on the present invention.

Figure 8:
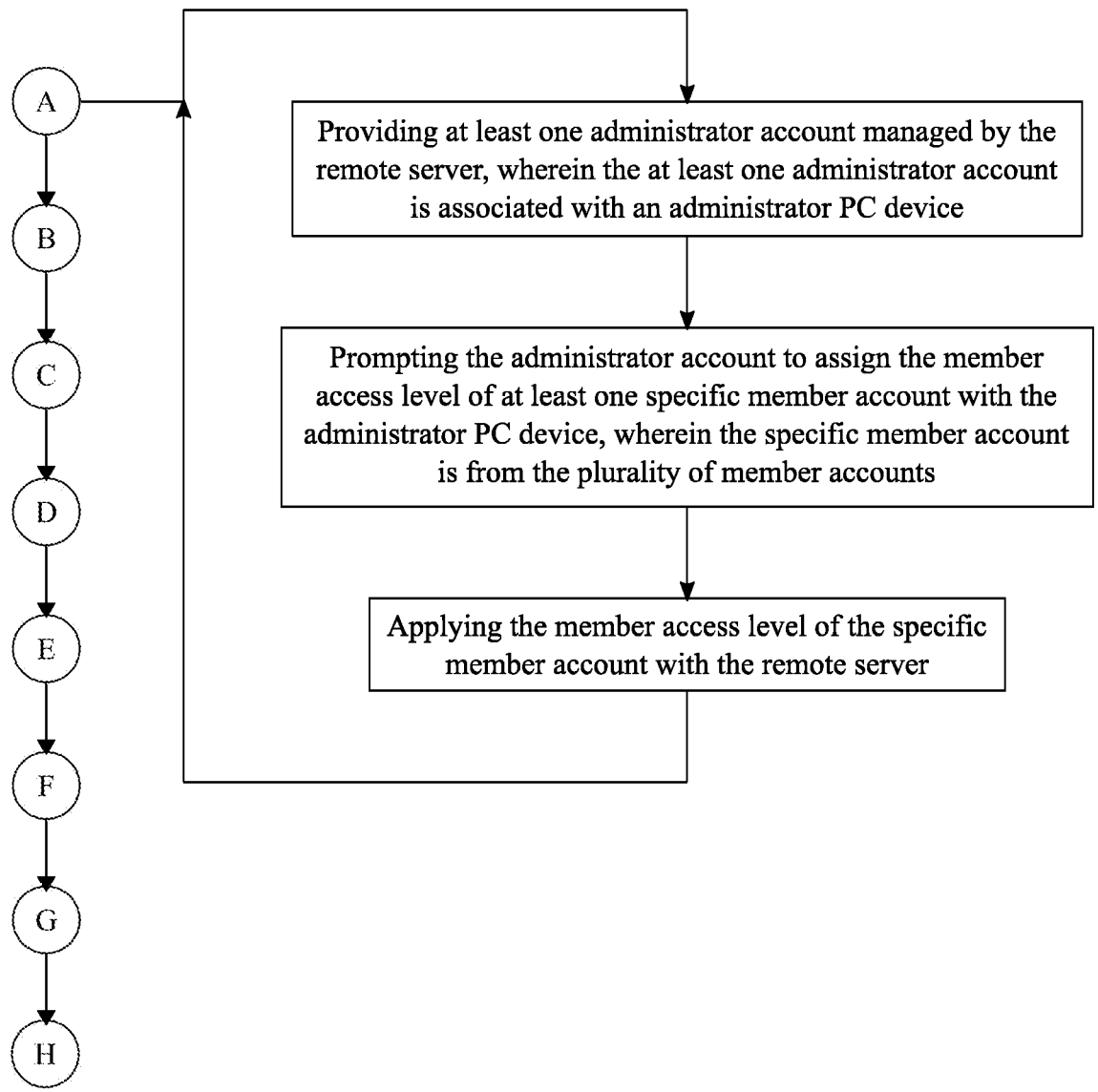
FIG. 8 is flowchart illustrating the subprocess of assigning of a member access level.

With reference to FIG. 8, the following subprocess is used to determine the member access level of a member account. The administrator account is prompted to assign the member access level of at least one specific member account with the administrator PC device. The specific member account is from the plurality of member accounts. This step allows the administrator account to assign the member access level after a new member account is created. The member access level of the specific member account is applied with the blockchain ledger. This step records and verifies the member access level of the specific member account.

Figure 9:
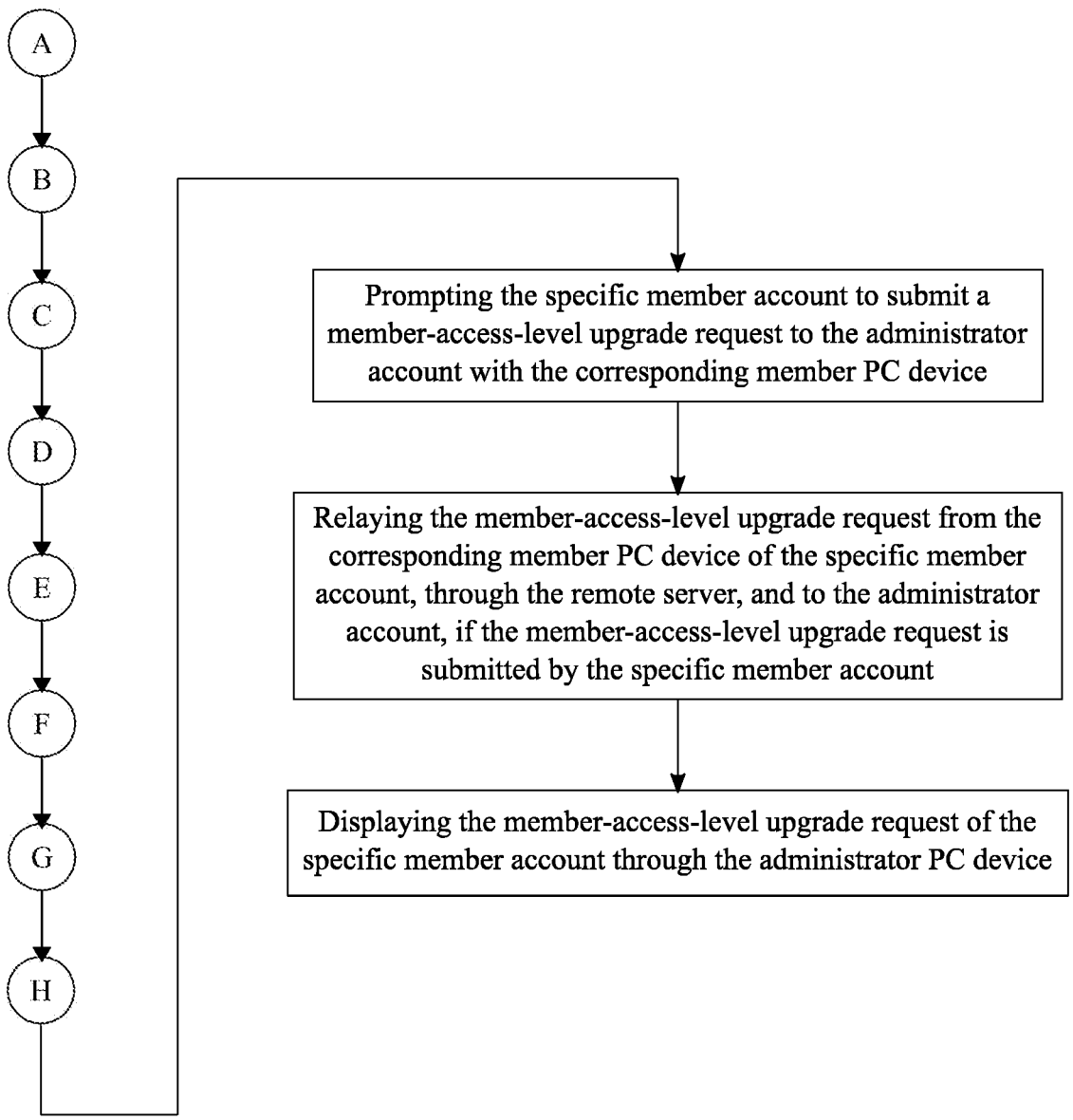
FIG. 9 is a flowchart illustrating the subprocess that allows a member account to request a member access level upgrade.

With reference to FIG. 9, the following subprocess allows a member account to upgrade the member access level. The specific member account is prompted to submit a member-access-level upgrade request to the administrator account with the corresponding member PC device. This step allows a user to request an upgrade to his or her member access level. The member-access-level upgrade request is relayed from the corresponding member PC device of the specific member account, through the remote server, and to the administrator account. This step is processed if the member-access-level upgrade request is submitted by the specific member account. This step notifies the administrator account that a user is attempting to upgrade his or her member access level. The member-access-level upgrade request of the specific member account is displayed through the administrator PC device. This step allows the administrator account to confirm the member-access-level upgrade request.

Figure 10:
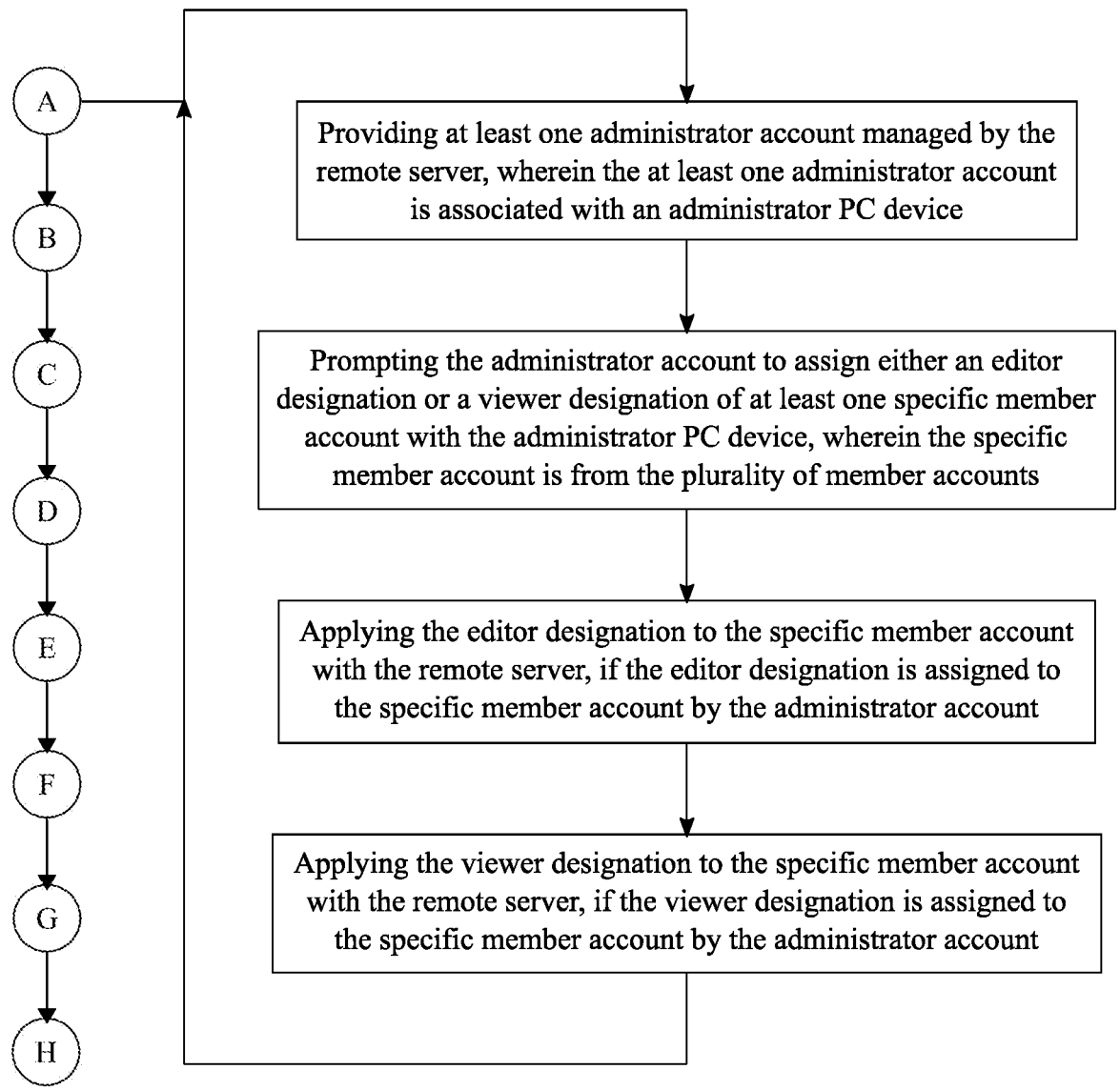
FIG. 10 is a flowchart illustrating the subprocess of assigning an editor or viewer designation.

With reference to FIG. 10, the following subprocess is used to designate a member account as an editor account or viewer account. The administrator account is prompted to assign either an editor designation or a viewer designation of at least one specific member account with the administrator PC device. The specific member account is from the plurality of member accounts. The editor designation designates a member account as an editor account which allows a user to upload or edit and to access files from the plurality of files. The viewer designation designates a member account as a viewer account which allows a user to access files from the plurality of files but does not allow a member account to upload or edit files from the plurality of files. The editor designation is applied to the specific member account with the remote server. This step is processed if the editor designation is assigned to the specific member account by the administrator account. Thus, a member account is now able to upload or edit files from the plurality of files. The viewer designation is applied to the specific member account with the remote server. This step is processed if the viewer designation is assigned to the specific member account by the administrator account. Thus, a member account is now able to access files from the plurality of files, but not allowed to upload or edit files from the plurality of files.

Figure 11:
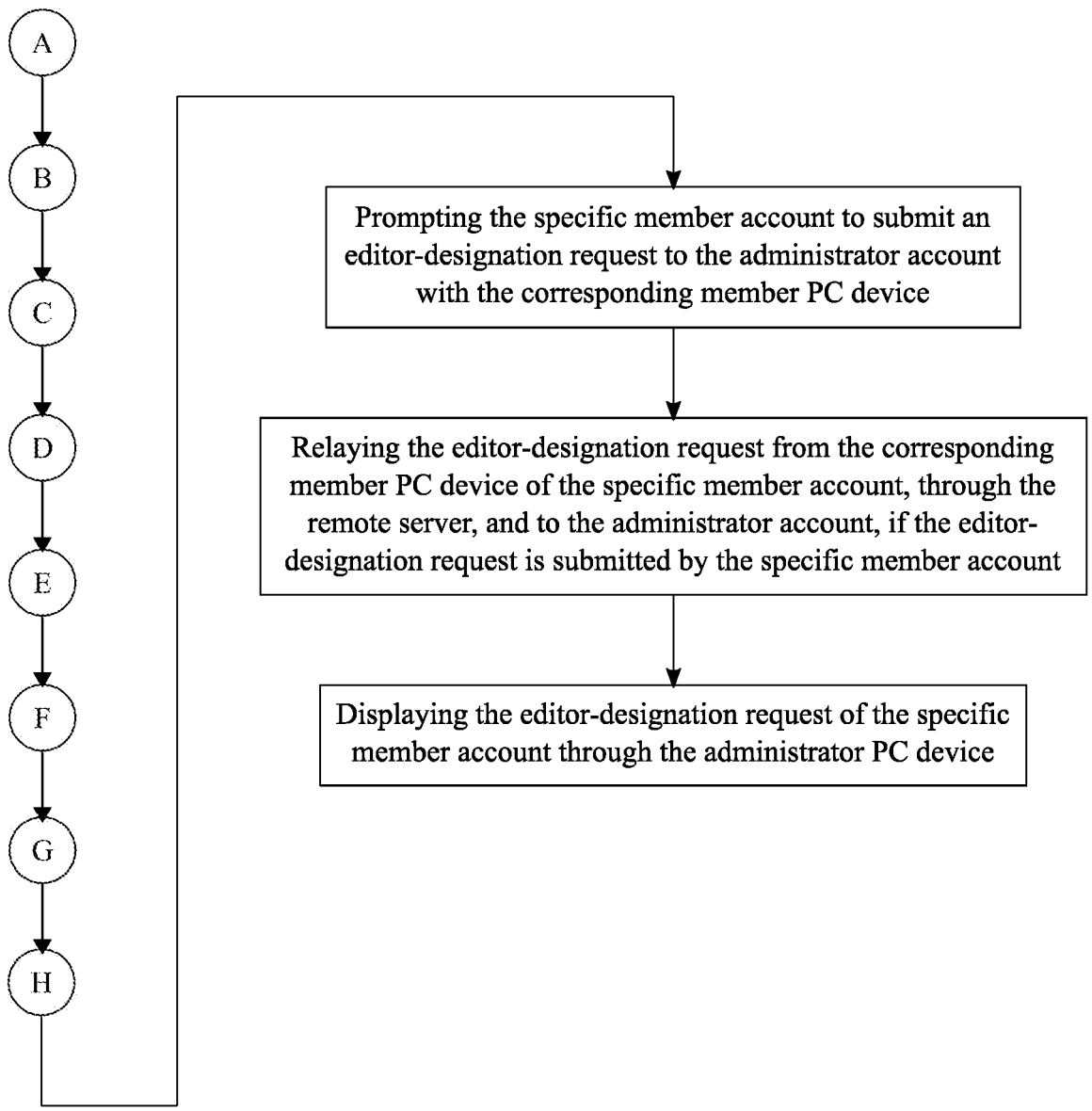
FIG. 11 is a flowchart illustrating the subprocess that allows a member account to request to be an editor account.

With reference to FIG. 11, the following subprocess allows a user to upgrade to an editor account. The specific member account is prompted to submit an editor-designation request to the administrator account with the corresponding member PC device. This step allows a user to request for an editor account. The editor-designation request is relayed from the corresponding member PC device of the specific member account, through the remote server, and to the administrator account. This step is processed if the editor-designation request is submitted by the specific member account. Further, this step notifies the administrator account that a user is attempting to upgrade to an editor account. After, the editor-designation request of the specific member account is displayed through the administrator PC device. Thus, this step allows the administrator account to confirm or deny the editor-registration request.

Figure 12:
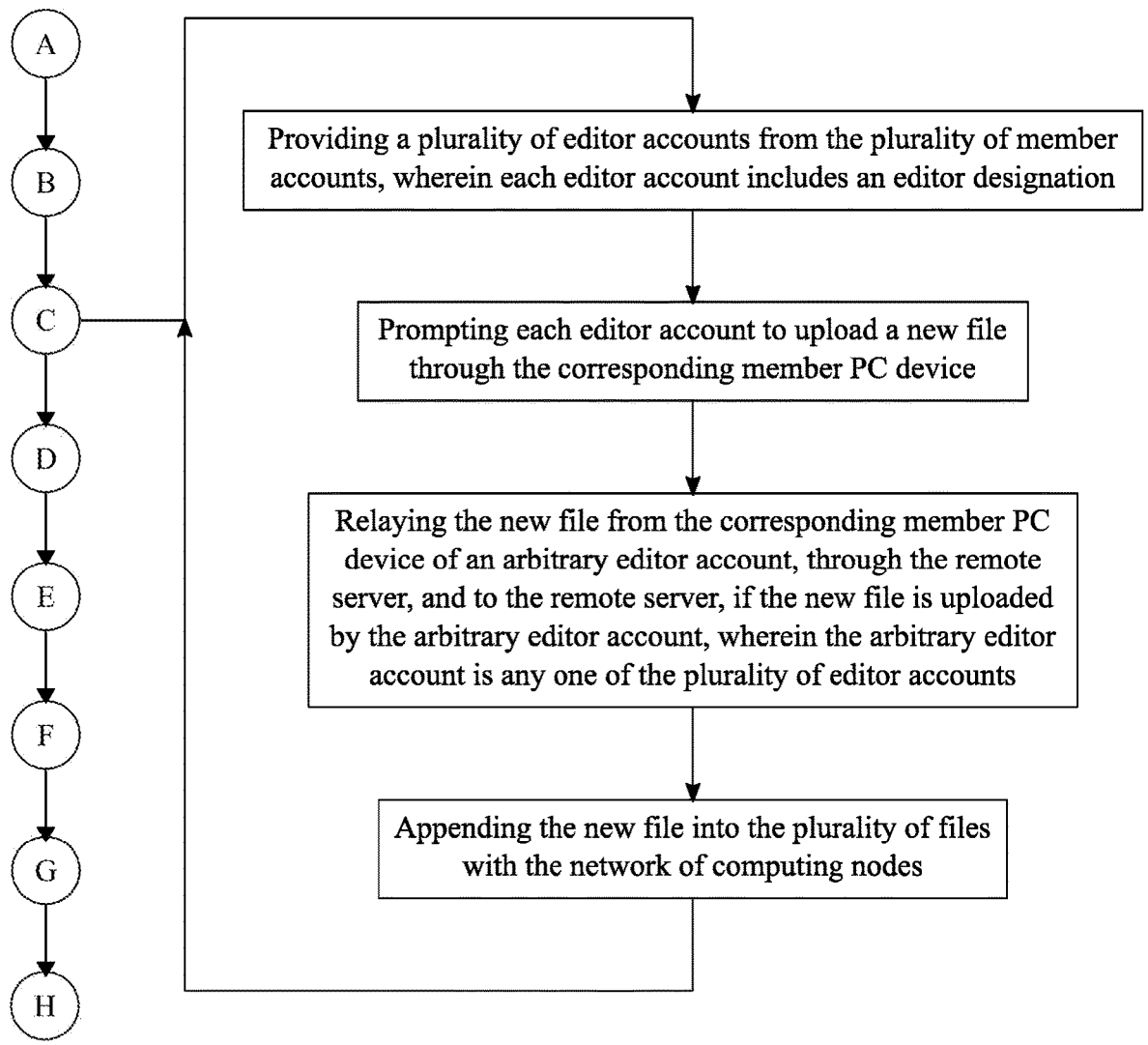
FIG. 12 is a flowchart illustrating the subprocess that allows an editor account to upload a new file.

With reference to FIG. 12, the following subprocess allows an editor account to upload a file into the plurality of files. Each editor account is prompted to upload a new file through the corresponding member PC device. This step gives each editor account to option to upload a new file into the plurality of files. The new file relayed from the corresponding member PC device of an arbitrary editor account, through the remote server, and to the remote server. This step is processed if the new file is uploaded by the arbitrary editor account. The arbitrary editor account is any one of the plurality of editor accounts. Thus, this step allows the remote server to receive the new file in order to include the new file into plurality of new files. The new file is appended into the plurality of files with the network of computing nodes. This step safely stores the new file and prevents any modification to the new file.

Figure 13:
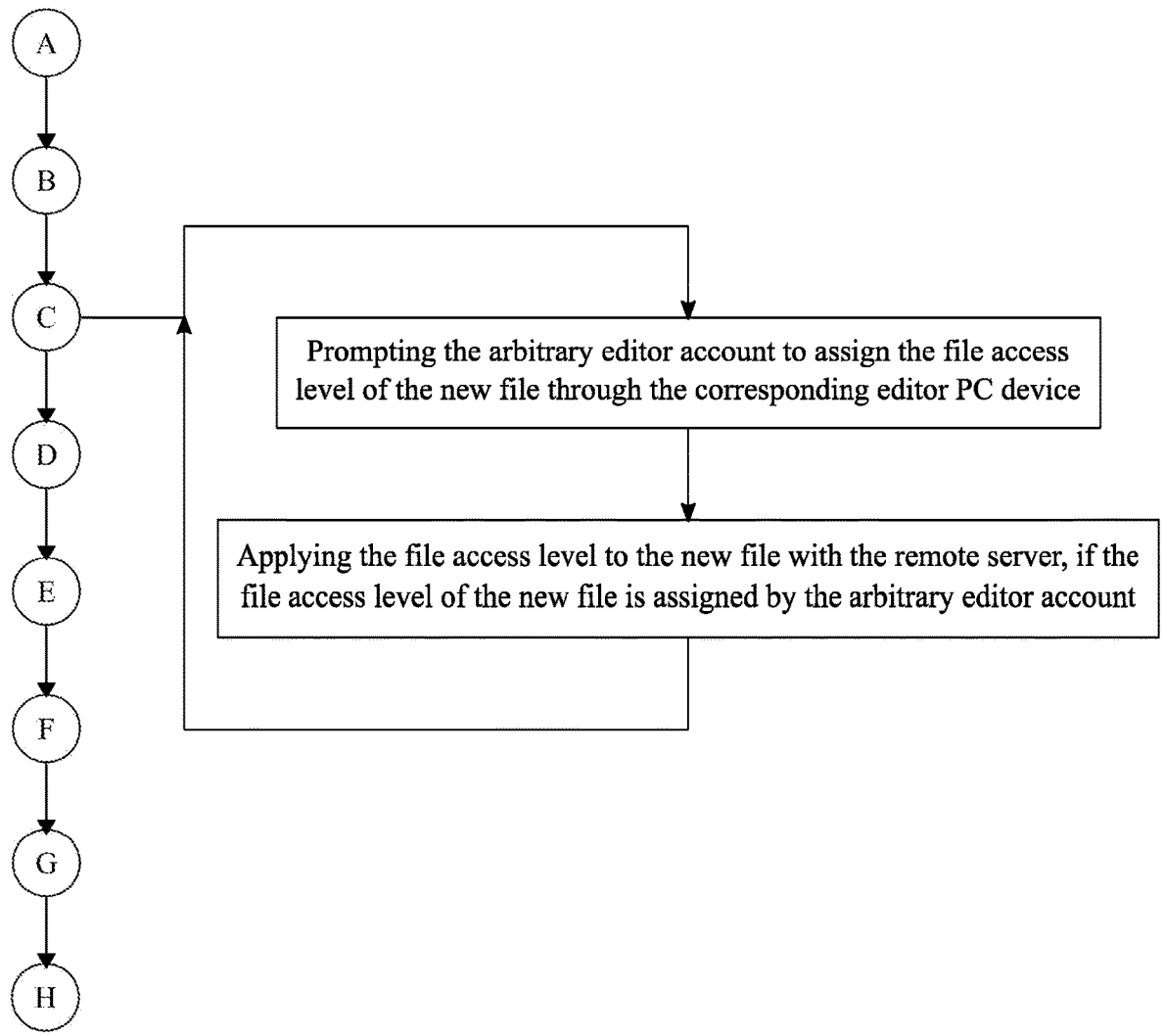
FIG. 13 is a flowchart illustrating the subprocess of assigning a file access level.

With reference to FIG. 13, the following subprocess allows an editor account to assign a file access level to a new file. The arbitrary editor account is prompted to assign the file access level of the new file through the corresponding editor PC device. This step provides an editor account the option to assign a file access level to a recently uploaded file. The file access level is applied to the new file with the remote server. This step is processed if the file access level of the new file is assigned by the arbitrary editor account. Further, this step protects the new file and allows only users, that meet specific requirements, to access the new file.

Figure 14:
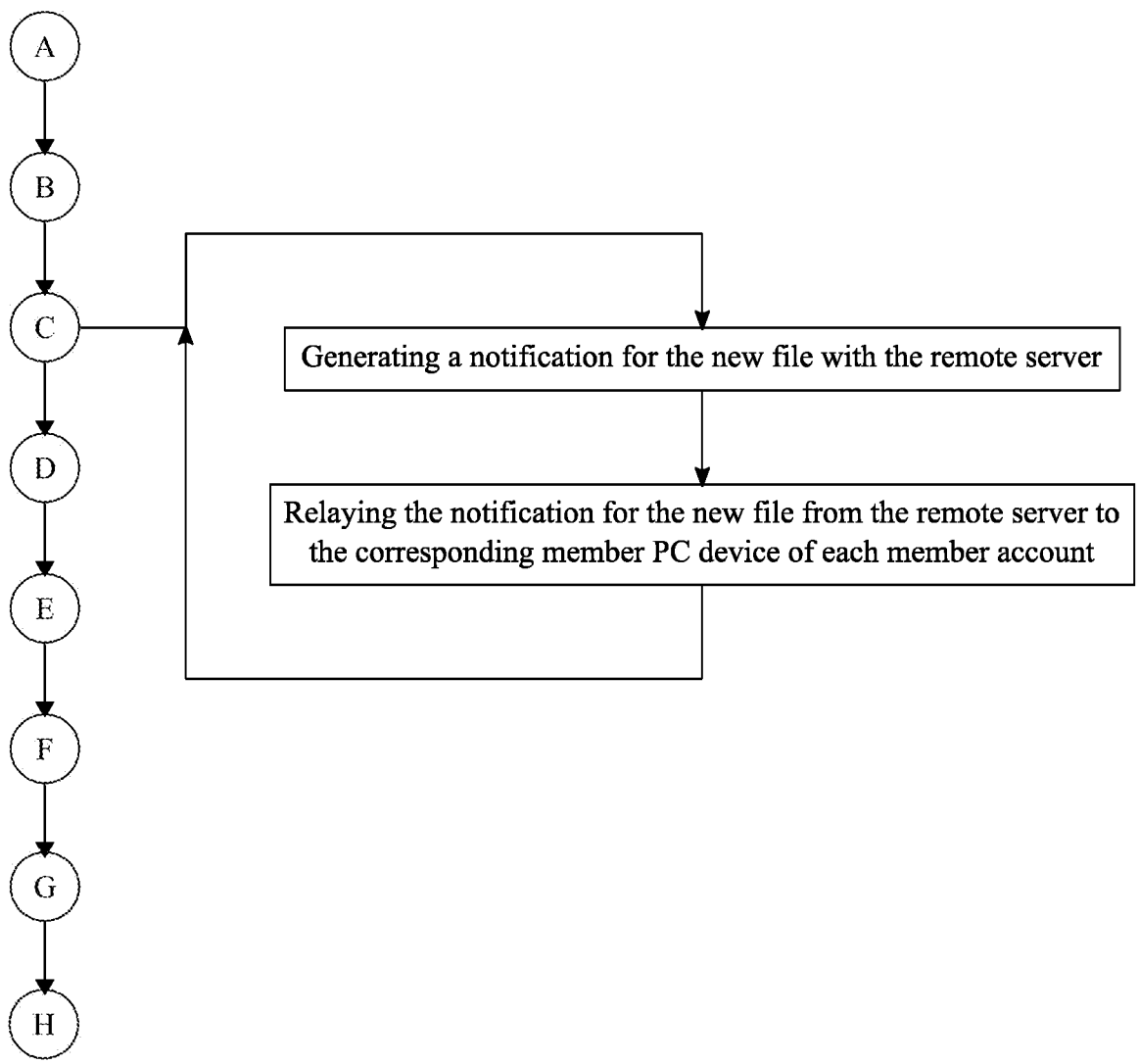
FIG. 14 is a flowchart illustrating the subprocess of notifying each member account that a new file has been uploaded.

With reference to FIG. 14, the following subprocess is used to notify each user that a new file has been uploaded. A notification for the new file is generated with the remote server. The notification for the new file includes information of the new file such as, but not limited to, the type of file, the file access level, and the name of the new file. Further, this step prepares the present invention in order to notify each user that a new file has been uploaded. The notification for the new file is relayed from the remote server to the corresponding member PC device of each member account. This step notifies each user that a new file has been uploaded.

Figure 15:
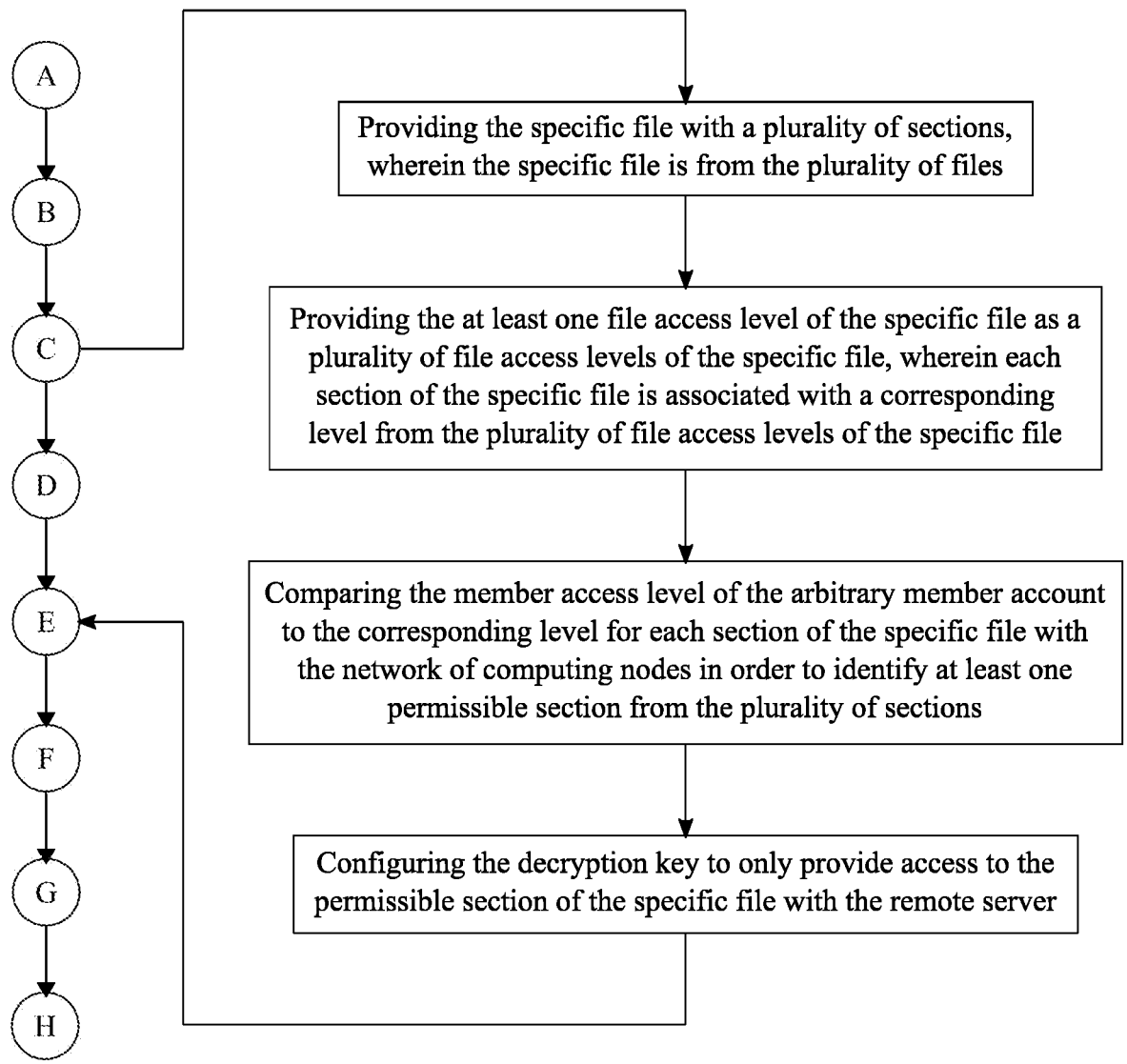
FIG. 15 is a flowchart illustrating the subprocess of permitting a member account to access sections of a file in accordance to the file access level of each section.

With reference to FIG. 15, the following subprocess is used to encrypt a file with multiple file access levels depending on the content of different sections of the file. The specific file is provided with a plurality of sections. The specific file is from the plurality of files. The at least one file access level of the specific file is provided as a plurality of file access levels of the specific file. Each section of the specific file is associated with a corresponding level from the plurality of file access levels of the specific file. For example, a document can contain many sections or pages. Further, specific sections or pages of the document may require a higher clearance in order for a user to access the specific sections or pages apart from the rest of the document. In order to identify at least one permissible section from the plurality of sections, the member access level of the arbitrary member account is compared to the corresponding level for each section of the specific file with the network of computing nodes. In further detail, this step determines which sections of a file or if the entire file can be accessed by a user. The decryption key is then configured to only provide access to the permissible section of the specific file with the remote server. In further detail, this step generates a decryption key which allows a user access only sections of a file or the entire file in accordance to the user's clearance level.

Figure 16:
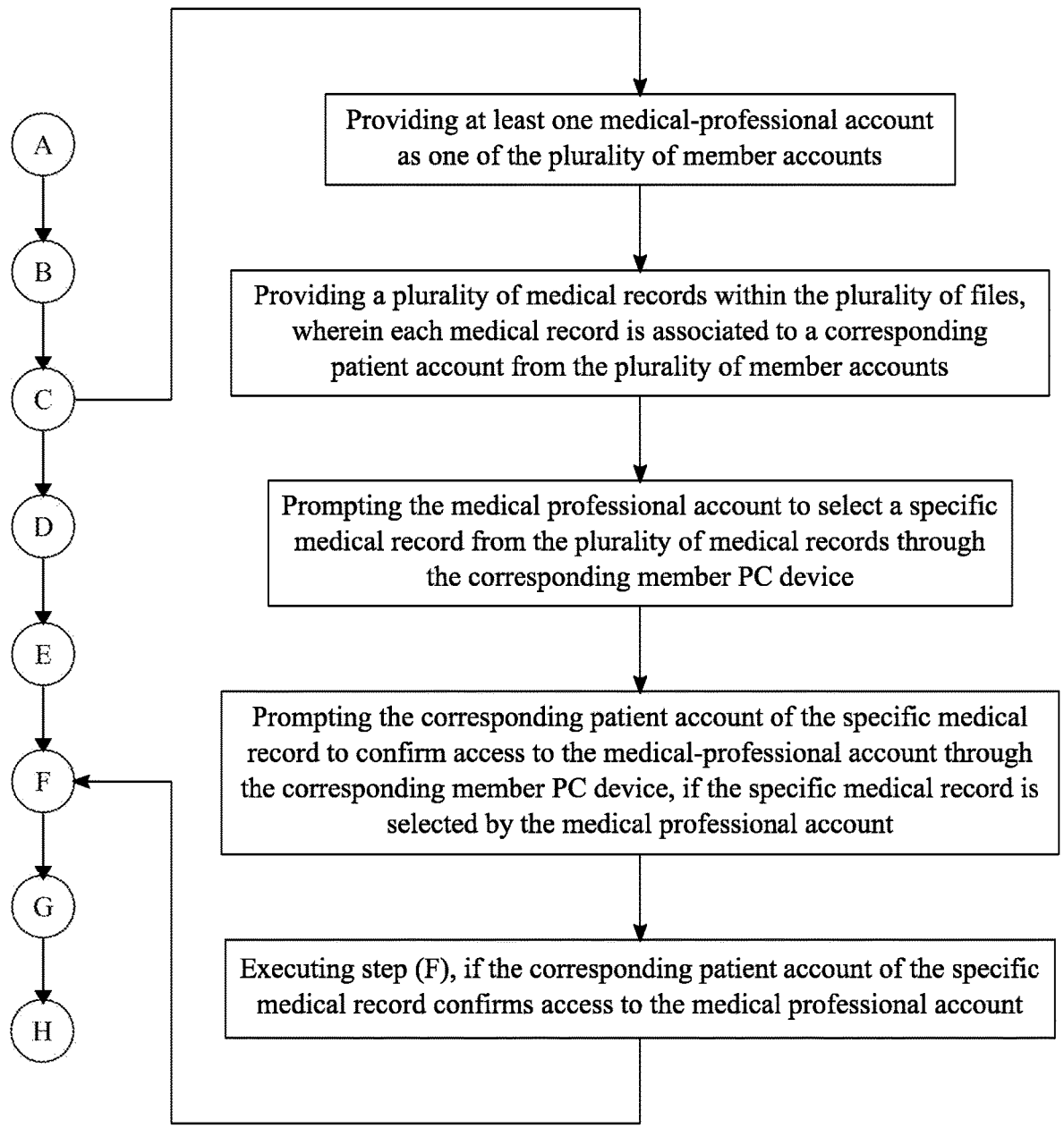
FIG. 16 is a flowchart illustrating the subprocess of a Health Insurance Portability and Accountability (HIPAA) compliance embodiment of the present invention.

With reference to FIG. 16, the following subprocess is used for a protected health information (PHI) embodiment of the present invention. In this embodiment, at least one medical-professional account is provided as one of the plurality of member accounts. Further, the plurality of files includes a plurality of medical records. Each medical record is associated to a corresponding patient account from the plurality of member accounts. A patient account is designated for a user who has stored medical records or PHI in the network of computing nodes. Furthermore, each medical record is PHI that is protected with Health Insurance Portability and Accountability (HIPAA) compliance. The medical professional account is designated for a user who is a medical professional such as a doctor or a HIPAA compliant. The medical professional account is prompted to select a specific medical record from the plurality of medical records through the corresponding member PC device. This step allows the medical professional account to select a medical record of a patient who has a member account. The corresponding patient account of the specific medical record is prompted to confirm access to the medical-professional account through the corresponding member PC device. This step is processed if the specific medical record is selected by the medical professional account. Further, this step allows a patient account to confirm or deny access to his or her PHI. Step F is executed if the corresponding patient account of the specific medical record confirms access to the medical professional account. This step allows the medical professional account to view the PHI of the corresponding patient account. Further, this step provides the required decryption key to the medical professional account in order to access the PHI of the corresponding patient.

Figure 17:
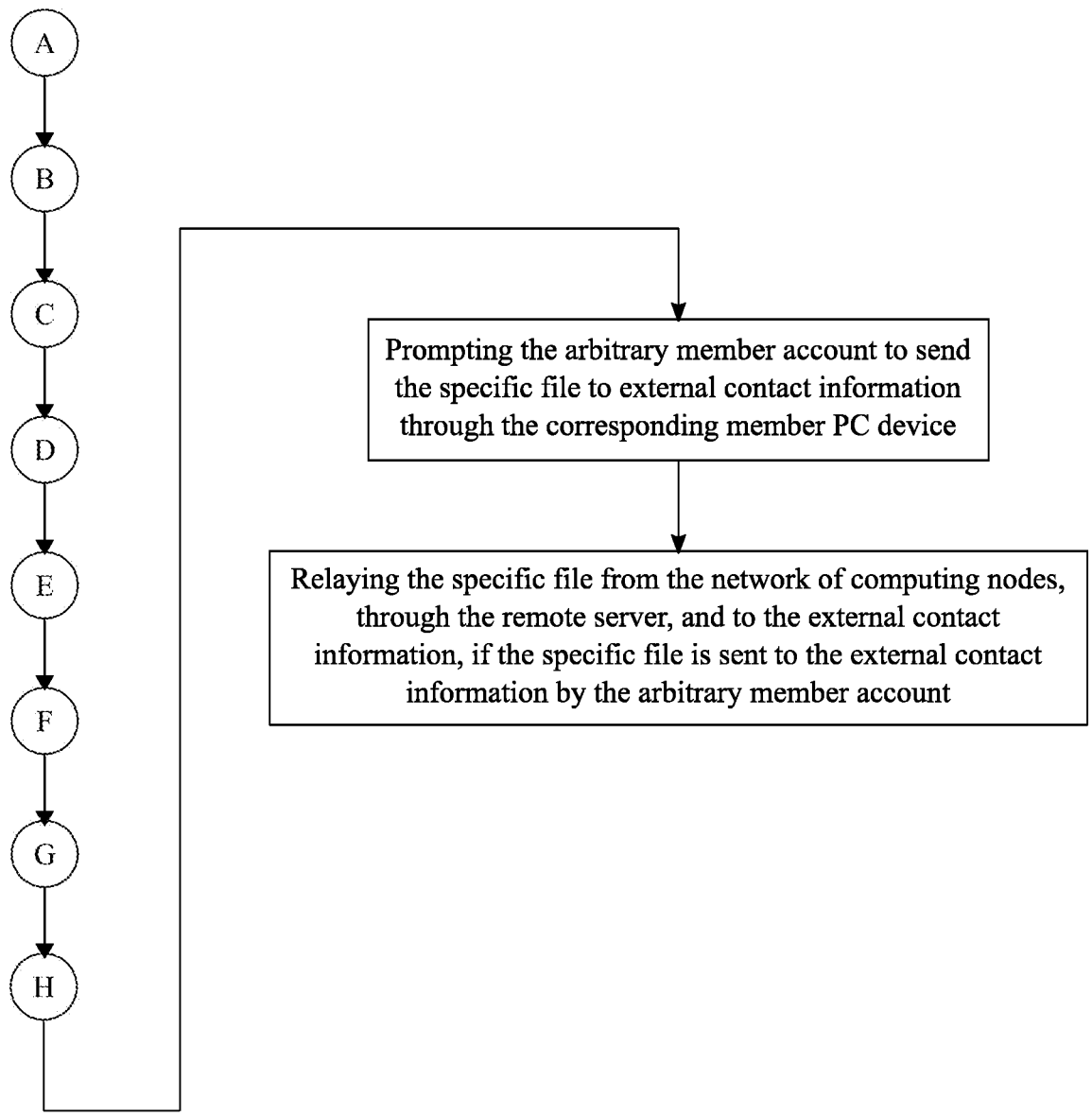
FIG. 17 is a flowchart illustrating the subprocess that allows a member account to share a file to an external contact.

With reference to FIG. 17, the following subprocess allows a user to share a file to an external individual. The arbitrary member account is prompted to send the specific file to external contact information through the corresponding member PC device. This step provides a user the option to share a file to an external individual who does not possess a member account on the present invention. Further, the external contact information may any type of contact information such as, but not limited to, an email address or a phone number. The specific file is relayed from the network of computing nodes, through the remote server, and to the external contact information. This step is processed if the specific file is sent to the external contact information by the arbitrary member account. Further, this step allows the individual of the external contract information to view a file chosen by a user with a member account.

Although the invention has been explained in relation to its preferred embodiment, it is to be understood that many other possible modifications and variations can be made without departing from the spirit and scope of the invention as hereinafter claimed.

What is claimed is:

1. A method of providing a secure inter-domain data management using blockchain technology, the method comprises the steps of:
    (A) providing at least one group managed by at least one remote server, wherein the at least one group includes a plurality of member accounts, and wherein each member account is associated with a corresponding member personal computing (PC) device and includes a member access level;
    (B) providing at least one blockchain system, wherein the blockchain system is managed by a network of computing nodes;
    (C) providing a plurality of files stored on the network of computing nodes, wherein each file includes at least one file access level;
    (D) prompting each member account to select a specific file from the plurality of files through the corresponding member PC device;
    (E) comparing the member access level of an arbitrary member account to the file access level of the specific file with the network of computing nodes in order to grant access to a decryption key for the specific file to the arbitrary member account, if the specific file is selected by the arbitrary member account in step (D), wherein the arbitrary member account is any one of the plurality of member accounts;
    (F) relaying the decryption key for the specific file from the network of computing nodes, through the remote server, and to the corresponding member PC device of the arbitrary member account, if the member access level of the arbitrary member account is greater than or equal to the file access level of the specific file;
    (G) prompting the arbitrary member account to enter the decryption key for the specific file into the blockchain system with the corresponding member PC device; and
    (H) accessing the specific file with the corresponding member PC device of the arbitrary member account, if the decryption key for the specific file is entered into the blockchain system in step (G).

2. The method of providing a secure inter-domain data management using blockchain technology, the method as claimed in claim 1 comprises the steps of:
    providing the at least one group as a plurality of groups, wherein each member account of each group includes a member group identifier, and wherein each file includes a file group identifier;
    providing the at least one blockchain system as a plurality of blockchain systems, wherein each group is associated with a corresponding blockchain system from the plurality of blockchain systems;
    comparing the member group identifier of the arbitrary member account to the file group identifier of the specific file with the network of computing nodes of the corresponding blockchain system in order to further grant access to the decryption key for the specific file to the arbitrary member account, if the specific file is selected by the arbitrary member account in step (D); and
    executing step (F), if the member group identifier of the arbitrary member account matches the file group identifier of the specific file.

3. The method of providing a secure inter-domain data management using blockchain technology, the method as claimed in claim 1 comprises the steps of:
    providing the at least one group as a plurality of groups, wherein each member account of each group includes a member group identifier, and wherein each file includes a file group identifier;
    prompting the arbitrary member account to select a specific blockchain system from the plurality of blockchain systems with the corresponding member PC device;
    relaying a selection for the specific blockchain system from the corresponding member PC device to the remote server, if the specific blockchain system is selected by the arbitrary member account; and
    displaying a list of the plurality of files from the network of computing nodes of the specific blockchain system with the corresponding member PC device before step (D).

4. The method of providing a secure inter-domain data management using blockchain technology, the method as claimed in claim 1 comprises the steps of:
    providing at least one administrator account managed by the remote server, wherein the at least one administrator account is associated with an administrator PC device;
    providing a member-account creation portal hosted on the remote server;
    prompting to submit a registration request through the member-account creation portal;
    relaying the registration request from the member-account creation portal to the administrator PC device;
    prompting the administrator account to confirm the registration request through the administrator PC device; and
    appending a new member account into the plurality of member accounts with the remote server, if the registration request is confirmed by the administrator account.

5. The method of providing a secure inter-domain data management using blockchain technology, the method as claimed in claim 1 comprises the steps of:
    providing at least one administrator account managed by the remote server, wherein the at least one administrator account is associated with an administrator PC device;
    providing a member-account creation portal hosted on the remote server;

prompting to submit a registration request through the member-account creation portal;

relaying the registration request from the member-account creation portal to the administrator PC device and to the corresponding member PC device of each member account;

prompting the administrator account and each member account to submit a confirmation/denial vote for the registration request through the administrator PC device and through the corresponding member PC device of each member account;

compiling the confirmation/denial vote for each member account and the confirmation/denial vote for the administrator account into a confirmation vote count and a denial vote count with the remote server; and appending a new member account into the plurality of member accounts with the remote server, if the confirmation vote count is greater than the denial vote count.

6. The method of providing a secure inter-domain data management using blockchain technology, the method as claimed in claim 1 comprises the steps of:

providing the specific file with a plurality of sections, wherein the specific file is from the plurality of files;

providing the at least one file access level of the specific file as a plurality of file access levels of the specific file, wherein each section of the specific file is associated with a corresponding level from the plurality of file access levels of the specific file;

comparing the member access level of the arbitrary member account to the corresponding level for each section of the specific file with the network of computing nodes in order to identify at least one permissible section from the plurality of sections; and configuring the decryption key to only provide access to the permissible section of the specific file with the remote server.

7. The method of providing a secure inter-domain data management using blockchain technology, the method as claimed in claim 1 comprises the steps of:

providing at least one medical-professional account as one of the plurality of member accounts;

providing a plurality of medical records within the plurality of files, wherein each medical record is associated to a corresponding patient account from the plurality of member accounts;

prompting the medical professional account to select a specific medical record from the plurality of medical records through the corresponding member PC device;

prompting the corresponding patient account of the specific medical record to confirm access to the medical-professional account through the corresponding member PC device, if the specific medical record is selected by the medical professional account; and executing step (F), if the corresponding patient account of the specific medical record confirms access to the medical professional account.

8. The method of providing a secure inter-domain data management using blockchain technology, the method as claimed in claim 1 comprises the steps of:

prompting the arbitrary member account to send the specific file to external contact information through the corresponding member PC device; and relaying the specific file from the network of computing nodes, through the remote server, and to the external contact information, if the specific file is sent to the external contact information by the arbitrary member account.

9. The method of providing a secure inter-domain data management using blockchain technology, the method as claimed in claim 1 comprises the steps of:

providing at least one administrator account managed by the remote server, wherein the at least one administrator account is associated with an administrator PC device;

prompting the administrator account to assign the member access level of at least one specific member account with the administrator PC device, wherein the specific member account is from the plurality of member accounts; and applying the member access level of the specific member account with the remote server.

10. The method of providing a secure inter-domain data management using blockchain technology, the method as claimed in claim 6 comprises the steps of:

prompting the specific member account to submit a member-access-level upgrade request to the administrator account with the corresponding member PC device;

relaying the member-access-level upgrade request from the corresponding member PC device of the specific member account, through the remote server, and to the administrator account, if the member-access-level upgrade request is submitted by the specific member account; and displaying the member-access-level upgrade request of the specific member account through the administrator PC device.

11. The method of providing a secure inter-domain data management using blockchain technology, the method as claimed in claim 1 comprises the steps of:

providing at least one administrator account managed by the remote server, wherein the at least one administrator account is associated with an administrator PC device;

prompting the administrator account to assign either an editor designation or a viewer designation of at least one specific member account with the administrator PC device, wherein the specific member account is from the plurality of member accounts;

applying the editor designation to the specific member account with the remote server, if the editor designation is assigned to the specific member account by the administrator account; and applying the viewer designation to the specific member account with the remote server, if the viewer designation is assigned to the specific member account by the administrator account.

12. The method of providing a secure inter-domain data management using blockchain technology, the method as claimed in claim 11 comprises the steps of:

prompting the specific member account to submit an editor-designation request to the administrator account with the corresponding member PC device;

relaying the editor-designation request from the corresponding member PC device of the specific member account, through the remote server, and to the administrator account, if the editor-designation request is submitted by the specific member account; and displaying the editor-designation request of the specific member account through the administrator PC device.

13. The method of providing a secure inter-domain data management using blockchain technology, the method as claimed in claim 1 comprises the steps of:

providing a plurality of editor accounts from the plurality of member accounts, wherein each editor account includes an editor designation;

prompting each editor account to upload a new file through the corresponding member PC device;

relaying the new file from the corresponding member PC device of an arbitrary editor account, through the remote server, and to the remote server, if the new file is uploaded by the arbitrary editor account, wherein the arbitrary editor account is any one of the plurality of editor accounts; and appending the new file into the plurality of files with the network of computing nodes.

14. The method of providing a secure inter-domain data management using blockchain technology, the method as claimed in claim 13 comprises the steps of:

prompting the arbitrary editor account to assign the file access level of the new file through the corresponding editor PC device; and applying the file access level to the new file with the remote server, if the file access level of the new file is assigned by the arbitrary editor account.

15. The method of providing a secure inter-domain data management using blockchain technology, the method as claimed in claim 13 comprises the steps of:

generating a notification for the new file with the remote server; and relaying the notification for the new file from the remote server to the corresponding member PC device of each member account.

\* \* \* \* \*